(12) United States Patent
Hong et al.

(10) Patent No.: US 7,225,661 B2
(45) Date of Patent: Jun. 5, 2007

(54) GAS SUPPLY ADAPTER

(75) Inventors: Soon Ho Hong, Seoul (KR); Je Yong Jin, Keungi-Do (KR)

(73) Assignees: Honeywell Analytics Limited, Poole (GB); Infitron, Inc., Seoul (KR)

( * ) Notice: Subject to any disclaimer, the term of this patent is extended or adjusted under 35 U.S.C. 154(b) by 168 days.

(21) Appl. No.: 10/526,348

(22) PCT Filed: Aug. 5, 2003

(86) PCT No.: PCT/GB03/03432

§ 371 (c)(1),
(2), (4) Date: Aug. 24, 2005

(87) PCT Pub. No.: WO2004/023135

PCT Pub. Date: Mar. 18, 2004

(65) Prior Publication Data

US 2006/0150711 A1     Jul. 13, 2006

(30) Foreign Application Priority Data

Sep. 3, 2002   (GB) ................................ 0220461.8

(51) Int. Cl.
G01N 21/00   (2006.01)
G08B 29/00   (2006.01)

(52) U.S. Cl. ...................................... 73/1.02; 340/515
(58) Field of Classification Search ........ 73/1.02–1.06, 73/856.6; 285/93, 901, 133.21, 371; 340/514, 340/515
See application file for complete search history.

(56) References Cited

U.S. PATENT DOCUMENTS 3,693,401 A * 9/1972 Purt et al. ..................... 73/1.05

4,374,329 A * 2/1983 Schoenfelder et al. ...... 250/574

(Continued)

FOREIGN PATENT DOCUMENTS

CA   2207117   6/1977

(Continued)

OTHER PUBLICATIONS

U.K. Search Report, Mar. 31, 2003.

(Continued)

Primary Examiner—Hezron Williams
Assistant Examiner—John Fitzgerald
(74) Attorney, Agent, or Firm—Welsh & Katz, Ltd.

(57) ABSTRACT

A single-piece adapter (10) is disclosed for supplying gas to a gas detector (32) that contains at least one gas sensor (34) and that has a gas inlet (30) for allowing gas at the inlet to come into contact with the at least one sensor (34), which adapter comprises: a chamber (24) having an opening formed by a rim (22) for fitting over the gas inlet of a gas detector (32), the chamber having an inner surface (18), an inlet duct (14) for feeding gas into the chamber in a direction transverse to the opening, and an outlet (16) to vent gases from within the chamber. The inner surface (18) of the chamber is formed by a first moulding (12) of a rigid, non-absorbent material and a second moulding (20) of resilient material. The second moulding forms the rim (22) for providing a gas-tight seal between the adapter (10) and the detector (32).

11 Claims, 4 Drawing Sheets

U.S. PATENT DOCUMENTS

| | | | | |
|---|---|---|---|---|
| 4,462,244 A | * | 7/1984 | Lee | 73/1.05 |
| 4,742,708 A | | 5/1988 | Porter | |
| 4,854,153 A | | 8/1989 | Miyagawa et al. | |
| 5,170,148 A | * | 12/1992 | Duggan et al. | 340/515 |
| 5,247,283 A | * | 9/1993 | Kobayashi et al. | 340/630 |
| 5,507,532 A | * | 4/1996 | Mitsui | 285/61 |
| 5,523,744 A | * | 6/1996 | Wieser | 340/630 |
| 5,670,946 A | * | 9/1997 | Ellwood et al. | 340/628 |
| 6,282,940 B1 | | 9/2001 | Hung et al. | |
| 6,423,962 B1 | * | 7/2002 | Pepper | 250/222.1 |
| 6,640,608 B2 | * | 11/2003 | Pepper et al. | 73/1.02 |
| 6,769,285 B2 | * | 8/2004 | Schneider et al. | 73/1.06 |

FOREIGN PATENT DOCUMENTS

| | | |
|---|---|---|
| EP | 0 319 933 | 6/1989 |
| EP | 503167 A1 * | 9/1992 |
| EP | 0 811 841 | 12/1997 |
| EP | 1 031 833 | 8/2000 |
| GB | 2 345 340 | 7/2000 |
| GB | 2 371 860 | 8/2002 |
| JP | 2006024064 A * | 1/2006 |
| WO | WO 9418653 A1 * | 8/1994 |

OTHER PUBLICATIONS

International Search Report, Nov. 12, 2003.

* cited by examiner

GAS SUPPLY ADAPTER

CROSS REFERENCE TO RELATED APPLICATION

The present application is the U.S. national stage application of International Application PCT/GB2003/003432, filed Aug. 5, 2003, which international application was published on Mar. 18, 2004 as International Publication WO 2004/023135. The International Application claims priority of British Patent Application 0220461.8, filed Sep. 3, 2002.

TECHNICAL FIELD

The present invention relates to the calibration of gas sensors and especially to an adapter for calibrating gas sensors, notably gas sensors in portable gas detectors (which term will be used for instruments for detecting or analysing gas or vapours). However, the present invention also extends to calibration adapters for fixed-installation gas detectors and to adapters for supplying samples of gas to a sensor for analysis or detection of gases present in an atmosphere, especially toxic gases and oxygen.

Gas detectors are used, for example, to detect or analyse potentially hazardous gases or vapours, e.g. hydrogen sulphide ($H_2S$), carbon monoxide (CO) and nitric oxides, and also oxygen and it is important that such instruments are correctly calibrated in order to provide accurate readings.

BACKGROUND ART

Gas detectors containing electrochemical gas sensors are well known for monitoring potentially hazardous environments, for example mines, tunnels, sewers and other closed environments. Such detectors are generally of the type in which gas from the atmosphere diffuses into contact with one or more sensors within a detector. Electronic circuits within the detector convert the output signal from each sensor into a reading of the amount of gas detected. The sensor output signal can drift and can also vary with the age of the sensor and hence periodic calibration is required to ensure that the detector output is accurate.

Safety regulations require that the sensors within a detector are tested on each occasion that they are taken into a potentially hazardous environment and that they are calibrated periodically according to the manufacturers' recommendations. Currently, such gas detector sensors are calibrated by passing a calibration gas of known composition from a compressed gas bottle at a predetermined flow rate through a pipeline to an adapter that fits over the gas inlet of the detector, i.e. the inlet in the detector that allows gas from the atmosphere being monitored to diffuse into contact with the sensors. Generally an excess of calibration gas is supplied to the adapter and a vent is provided to atmosphere in order to prevent the pressure in the adapter from building up.

An example of a calibration adapter is disclosed in U.S. Pat. No. 4,854,153 in which a gas detector is shown that is pressed against a calibration adapter and sealed thereto by an O-ring. Gas is fed into a chamber within the adapter that is in contact with the gas inlet of the detector; an outlet vent is also provided from the chamber.

GB 2 345 340 disclosures a hood for surrounding a wall-mounted gas detector for providing an isolated environment into which calibration gas is fed.

EP 0 319 933 discloses a calibration valve for an oxygen sensor in a respiratory gas system.

U.S. Pat. No. 4,742,708 describes a calibration cap that is attached to a sensor by hook and loop fabric, e.g. Velcro® fabric.

U.S. Pat. No. 6,282,940 describes a device for testing carbon monoxide sensors, including a housing made of clear plastic that fits over the carbon monoxide detector.

Calibration adapters should provide the calibration gas to the sensors in a way that mimics as closely as possible the diffusion of gas that occurs during normal operation of the detector when monitoring an open atmosphere.

One problem associated with calibration adapters is that they should use a compliant material to provide a good seal against the gas detector to prevent extraneous atmospheric gas from entering the chamber within the calibration adapter. On the other hand, compliant material, e.g. natural rubber, can both absorb elements within the calibration gas (and so reduce the amount of that component in the calibration gas) and also be degraded by some components of calibration gases. Inert compliant materials are known but they tend to be expensive.

DISCLOSURE OF INVENTION

According to the present invention, there is provided a single-piece adapter for supplying gas to a gas detector that contains at least one gas sensor and that has a gas inlet for allowing gas at the inlet to come into contact with the at least one sensor, which adapter comprises:

a chamber having an opening for fitting over the gas inlet of a gas detector, the chamber having an inner surface, an inlet duct for feeding gas into the chamber in a direction transverse to the opening, and an outlet to vent gases from within the chamber, wherein the inner surface of the chamber is formed by a first moulding of a rigid, non-absorbent material and a second moulding of resilient material and wherein the second moulding forms the part of the surface surrounding the said opening.

The interface between the first and the second mouldings may be arranged to engage the gas detector form a seal isolating the chamber from the ambient atmosphere.

Because the resilient material is provided only around the lower part of the inner surface surrounding the opening, while the rest of the inner surface of the chamber is formed from the first moulding, only a very limited amount of the second moulding is exposed to the calibration gas in the chamber and preferably only the edge of the interface between the first and second mouldings is exposed to the gas within the chamber. Thus the vast majority of the inner surface of the adapter chamber is provided by the hard non-absorbent plastics material of the first moulding and accordingly the amount of gas that can be absorbed by, or that can degrade, the resilient material is minimal. In addition, the resilient material provides a good gas-tight seal merely by placing the adapter on the gas detector without having to apply pressure to the adapter to keep it in contact with the gas detector.

In addition to providing calibration, adapters can also be used to supply a sample of gas to a gas detector from an atmosphere being monitored.

Preferably, the gas inlet duct and gas outlet are in line with each other and a baffle is provided between the inlet and the outlet to prevent gas passing directly from the inlet to the outlet.

In order to prevent build up of pressure within the adapter chamber, the cross sectional area of the outlet is preferably greater than the cross sectional area of the inlet duct. The outlet may be a simple opening to atmosphere or may be a duct for removing possibly toxic material and hence preventing the immediate atmosphere surrounding the gas detector from being filled with toxic calibration gas.

The second moulding of compliant material preferably extends over the whole of the outer surface of the adapter and the adapter is preferably formed by over-moulding the first moulding with the second moulding.

The present invention also provides a method of using the adapter to feed gas to a detector.

BRIEF DESCRIPTION OF DRAWINGS

A calibration adapter in accordance with the present invention will now be described, by way of example only, with reference to the accompanying drawings in which.

PREFERRED MODE FOR PUTTING THE INVENTION INTO OPERATION

Figure 1:
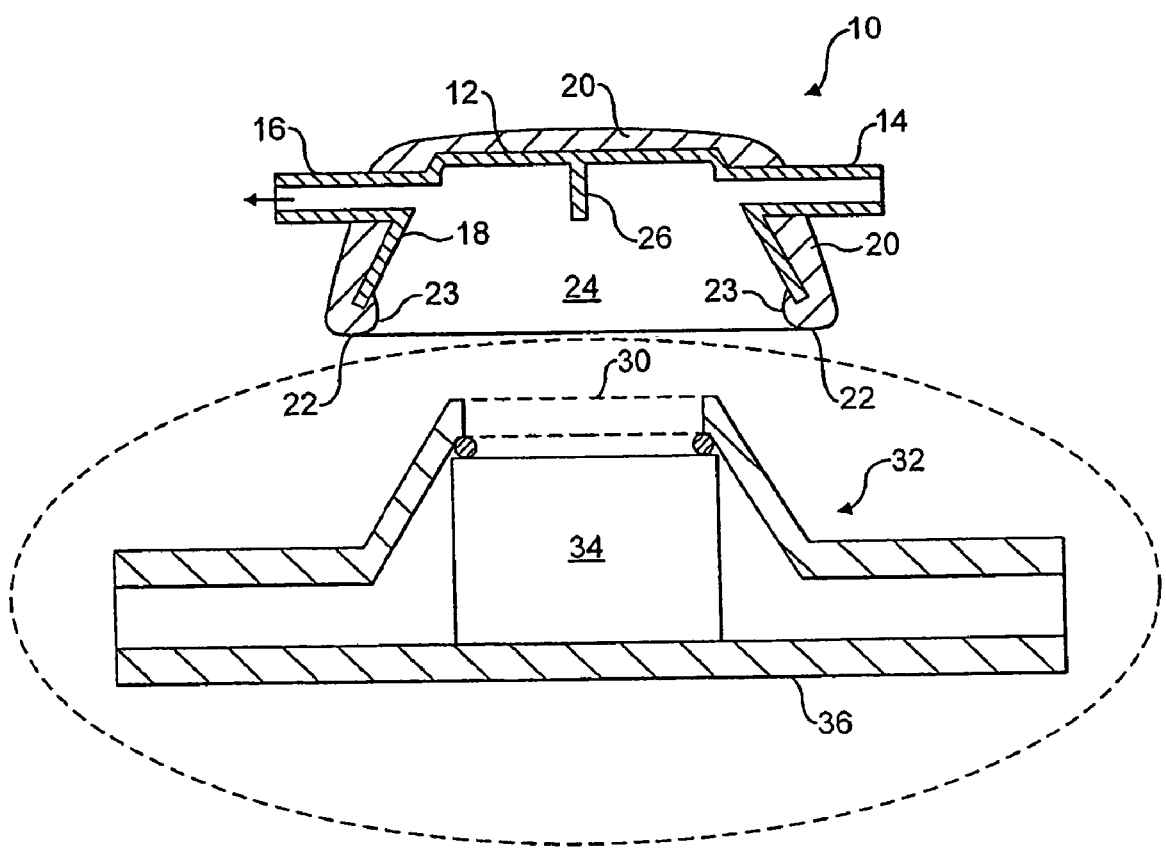
FIG. 1 is a schematic view showing the operation of the adapter of the present invention.
Figure 2:
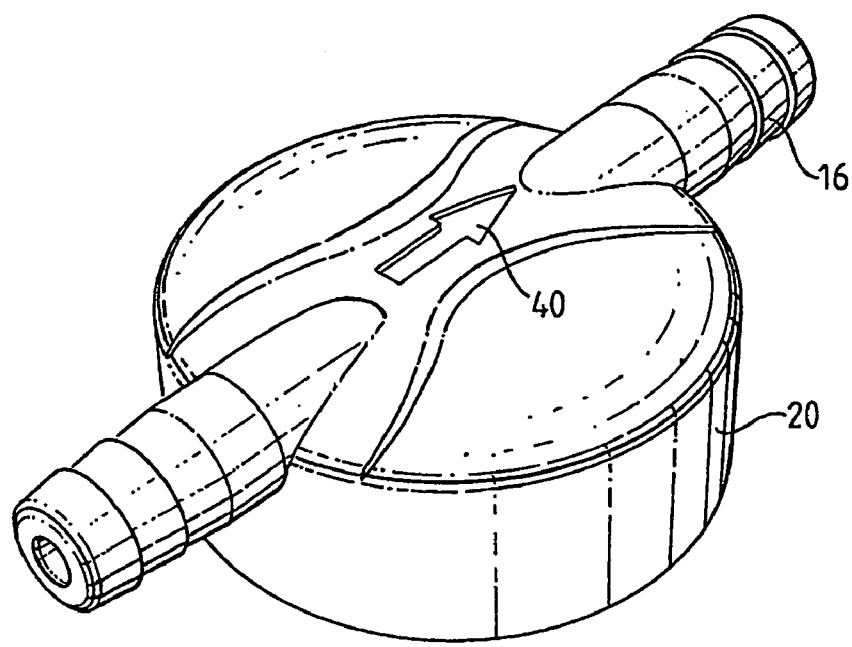
FIG. 2 is a picture of the adapter of the present invention.

Referring initially to FIG. 1, there is shown a schematic cross section of the adapter 10, which includes a first moulding 12 (shown by thick black lines) formed of an inert rigid plastic that does not absorb gas, e.g. ABS. It includes an inlet 14 and an outlet 16 for calibration gas. The first moulding 12 has a skirt 18.

The first moulding 12 is incorporated into a further mould and a second moulding 20 is made around the first moulding. The second moulding surrounds the outer surface of the first moulding, forms a bottom rim 22 of the adapter and extends part of the way up the internal surface of the skirt 18.

Thus, the adapter has an internal chamber 24 that can be supplied with calibration gas through inlet 14 and vented through outlet 16. In order to avoid pressure building up in the chamber 24, the cross sectional area of the outlet 16 is greater than the cross sectional area of the inlet 14. The inlet 14 is connected by a hose (not shown) to a source of compressed calibration gas via a valve (not shown) providing a constant flow of gas. The inlet and outlet 14, 16 are arranged in line transversely to the open bottom face of the adapter formed by rim 22. The inlet and outlet are provided in line and in order to prevent gas flowing directly from the inlet to the outlet, a baffle 26 is provided that causes gas passing through the inlet to circulate within the chamber 24 and hence diffuse to a calibration sensor, as described later. Such an arrangement prevents calibration gas being directly directed onto the sensor, which could give rise to inaccurate sensor readings.

The calibration cap 10 is designed to fit over a gas aperture 30 in a gas detector housing 32. The gas aperture is in gaseous contact with a sensor 34 seated on the printed circuit board 36 within the detector; the printed circuit board 36 receives signals from the sensor and processes them to give an output in accordance with the amount of gas detected by the sensor.

The internal face of the skirt 18 is designed to fit over the detector housing 32. The second moulding that forms the rim 22 and extends part of the way up the internal surface of the skirt 18 provides a gas-tight seal against the detector housing 32 without having to apply external pressure to the adapter 10. However, clips or other devices that keep the adapter 10 fast against the detector housing 32 can be provided if desired.

Because only the edge 23 of the second moulding 20 is in contact with the atmosphere within the chamber 24 containing calibration gas, the soft compliant rubber of the second moulding has little capacity for absorbing calibration gas. The inner surface of the chamber 24 that contacts the calibration gas is otherwise formed by the first moulding 12, which cannot absorb the calibration gas.

Figure 3:
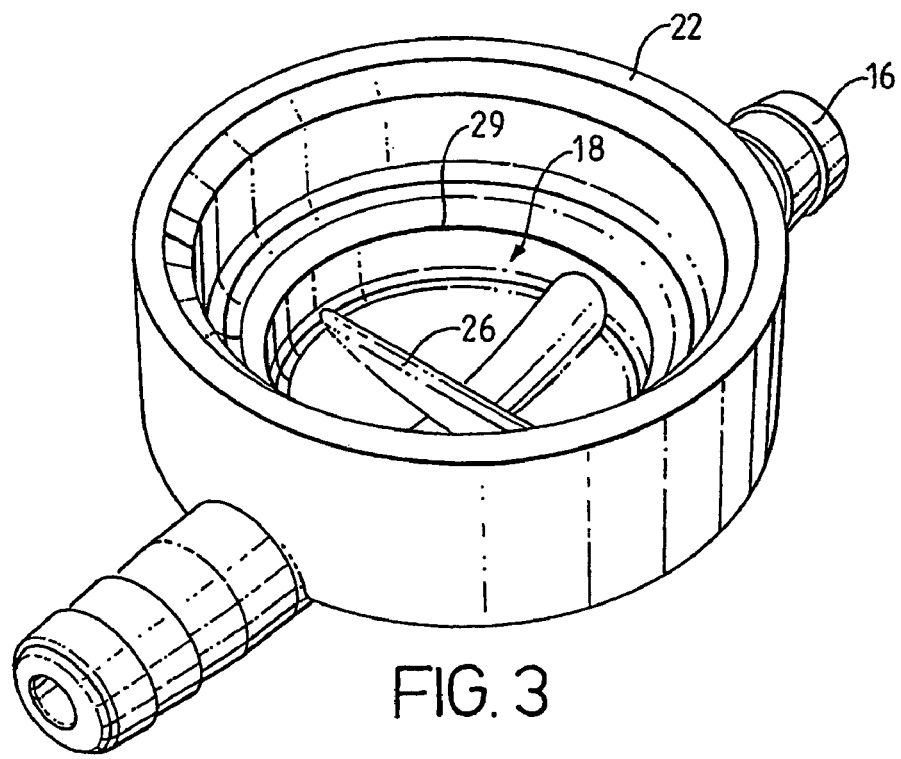
FIG. 3 is a picture showing the inside of the adapter of FIG. 2.

An adapter is shown in FIGS. 2 to 5; the first moulding is shown in a grey colour and the second moulding in black. As can be seen from FIG. 2, the inlet and outlet 14, 16 are formed from the first moulding but otherwise the whole of the external surface of the adapter is formed of the second moulding 20, apart from an arrow 40, which shows the direction of gas flow within the adapter from the inlet 14 to the outlet 16. The inside of the adapter is shown in FIG. 3. As can be seen, the second mould extends up the side wall 18 of the first moulding. The edge 29 of the second moulding will rest against the detector housing 32 and so only the edge 29 of the said moulding is exposed to calibration gas. The baffle 26 is also clearly visible between the inlet and outlet 14, 16.

Because the inlet and outlet 14, 16 are formed by the rigid plastic material of the first moulding, it is relatively easy to push a tubing onto the inlet and outlet.

If the calibration gas is toxic, then the tubing attached to the outlet 16 can conduct the gas away for safe method disposal.

Figure 5:
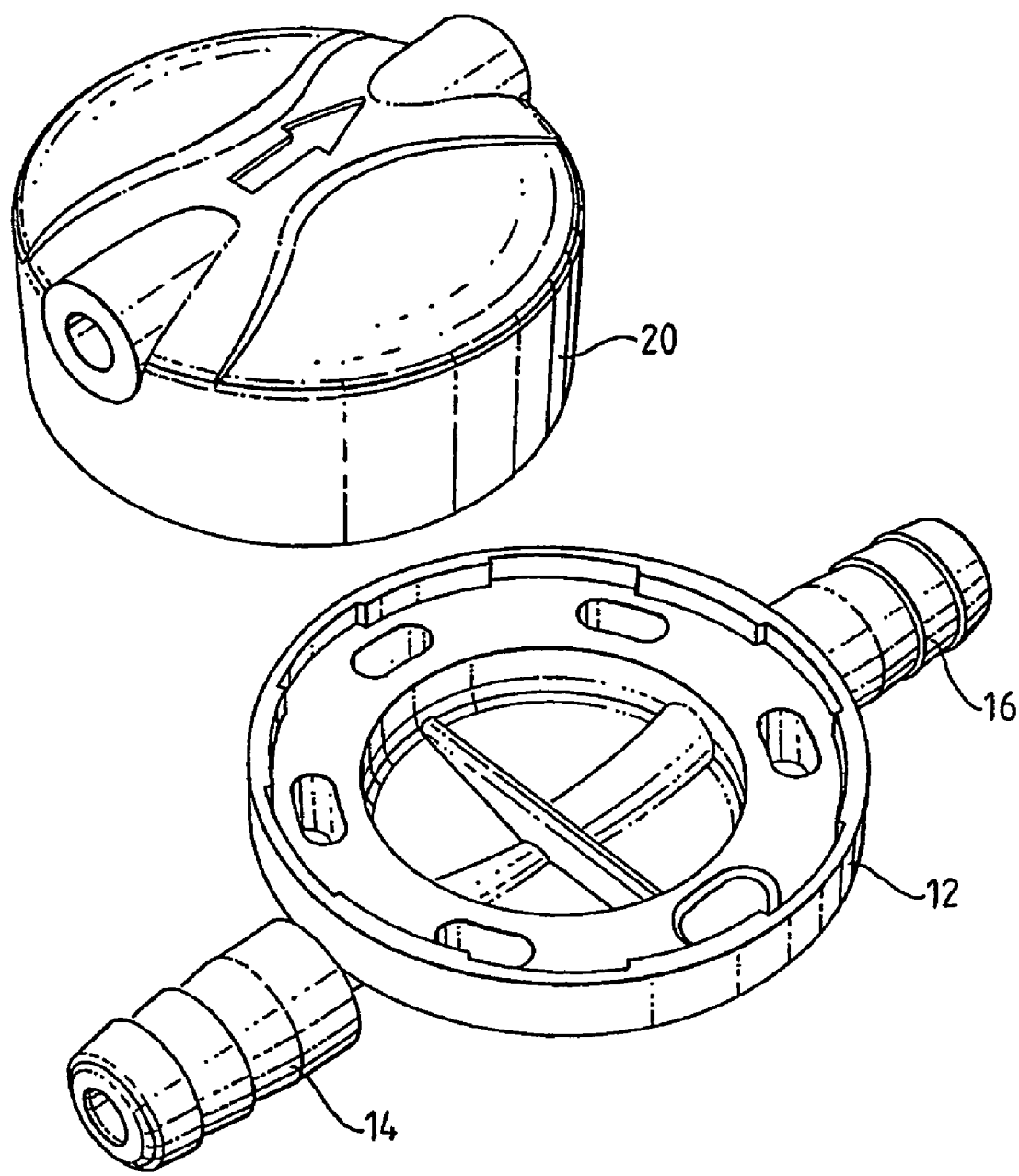
FIG. 5 is a picture similar to FIG. 4 but showing the inside of one of the parts of the moulding.

As can be seen in FIG. 5, the diameter of the outlet 16 is substantially larger than the diameter of the inlet 14 in order to allow unrestricted flow of calibration gas from out of the chamber 24 to prevent pressure build up in the chamber, which could effect the calibration results.

Figure 4:
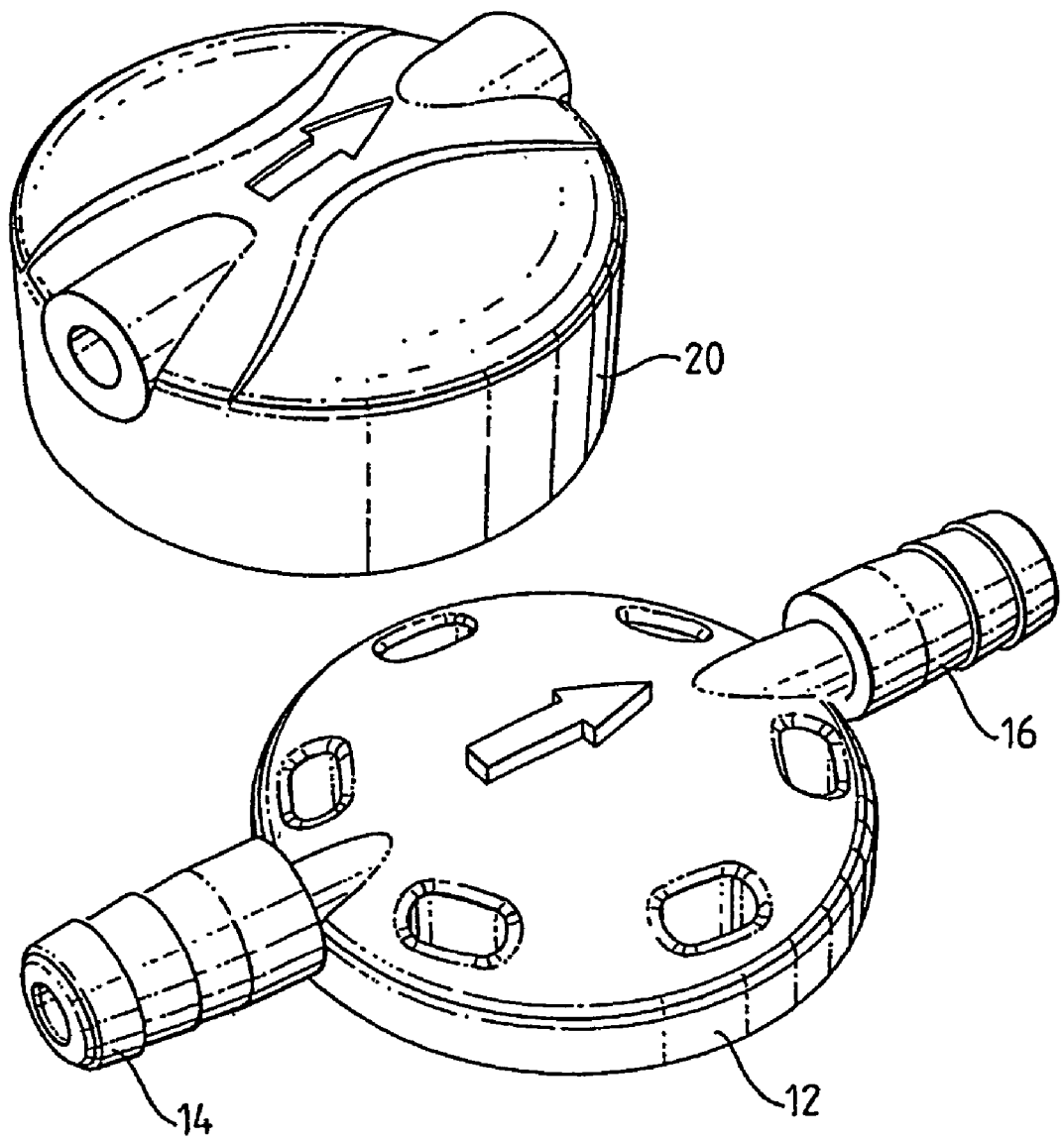
FIG. 4 is a picture of the two parts of the moulding making up the adapter of FIGS. 2 and 3.

It should be appreciated that the moulding parts shown in FIGS. 4 and 5 do not ever exist independently since they are made in a two-part moulding process as described.

Because a rigid plastic is used as the first moulding, which provides a skeleton to the calibration adapter, the calibration adapter retains its shape well and provides consistent sealing to a detector during calibration. The skeleton configuration also makes the handling of the detector easier. On the other hand, the compliant, resilient, second moulding provides compliant sealing against the detector housing and can also adapt to minor dimensional variations in the detector housing. Furthermore, the compliant second moulding means that there is no mechanical damage or scratching to the detector housing while the adapter is mounted or dismounted.

The invention claimed is:

1. A single-piece adapter for supplying gas to a gas detector that contains at least one gas sensor and that has a gas inlet for allowing gas at the inlet to come into contact with the at least one sensor, which adapter comprises:

a chamber having an opening for fitting over the gas inlet of a gas detector, the chamber having an inner surface, an inlet duct for feeding gas into the chamber in a direction transverse to the opening, and an outlet to vent gases from within the chamber, wherein the inner surface of the chamber is formed by a first moulding of a rigid, non-absorbent material and a second moulding of resilient material and wherein the second moulding forms the part of the surface surrounding the said opening.

2. An adapter as claimed in claim 1, wherein the interface between the first and the second mouldings on the inner chamber wall is arranged to engage the gas detector to form a seal isolating the chamber from the ambient atmosphere.

3. An adapter as claimed in claim 1, wherein only the edge of the interface between the first and second mouldings is exposed to the gas within the chamber.

4. An adapter as claimed in claim 1, wherein the gas inlet duct and the gas outlet are in line with each other and a baffle is provided between the inlet duct and the outlet to prevent gas passing directly from the inlet to the outlet.

5. An adapter as claimed in claim 1, wherein the cross sectional area of the outlet is greater than the cross sectional area of the inlet duct.

6. An adapter as claimed in claim 1, wherein the second moulding of resilient material extends substantially over the whole of the outer surface of the adapter, except for the inlet duct and the outlet.

7. An adapter as claimed in claim 1, wherein the second moulding is an over-moulding of the first moulding.

8. A method of supplying gas to a gas detector that contains at least one gas sensor and that has a gas inlet for allowing gas at the inlet to come into contact with the at least one sensor, which method comprises providing an adapter that comprises a chamber having an opening, a gas inlet duct and an outlet, placing the opening of the adapter over the gas inlet of the gas detector to form a seal between the adapter and the detector to isolate the chamber from the atmosphere, wherein the inner surface of the chamber is formed by a first moulding of a rigid, non-gas absorbent material and a second moulding of resilient material, the second moulding forming the part of the surface surrounding the said opening.

9. A method as claimed in claim 8, wherein the interface between the first and the second mouldings on the inner chamber surface engages the gas detector to form the seal isolating the chamber from the ambient atmosphere.

10. A method as claimed in claim 9, wherein only the edge of the interface between the first and second mouldings is exposed to the gas within the chamber.

11. A method as claimed in claim 8, wherein the gas inlet duct and the gas outlet are in line with each other and a baffle is provided between the inlet duct and the outlet to prevent gas passing directly from the inlet to the outlet.

* * * * *